United States Patent [19]

Iwami et al.

[11] 4,156,618
[45] May 29, 1979

[54] PROCESS FOR SEPARATING KETOSES AND ALDOSES

[75] Inventors: Isamu Iwami, Zushi; Toshio Asano, Nobeoka; Masami Yamaguchi, Tokorozawa, all of Japan

[73] Assignee: Asahi-Dow Limited, Tokyo, Japan

[21] Appl. No.: 829,492

[22] Filed: Aug. 31, 1977

[30] Foreign Application Priority Data

Sep. 7, 1976 [JP] Japan .................................. 51-106245
Dec. 27, 1976 [JP] Japan .................................. 51-156251
Dec. 27, 1976 [JP] Japan .................................. 51-156252

[51] Int. Cl.$^2$ ...................... C13D 3/14; C13K 1/00; C13K 3/00; C13K 11/00
[52] U.S. Cl. .................................................. 127/46 A
[58] Field of Search ........................... 127/46 A, 46 B

[56] References Cited

U.S. PATENT DOCUMENTS

| | | | |
|---|---|---|---|
| 2,681,319 | 6/1954 | Bodamer | 127/46 A X |
| 2,813,810 | 11/1957 | Smith et al. | 127/46 R |
| 3,044,904 | 7/1962 | Serbia | 127/46 B |
| 3,044,905 | 7/1962 | Lefevre | 127/46 B |
| 3,416,961 | 12/1968 | Mountfort et al. | 127/46 A |
| 3,471,329 | 10/1969 | Quletensky et al. | 127/46 |
| 3,806,363 | 4/1974 | Takasaki | 127/46 A |
| 4,022,637 | 5/1977 | Sutthoff | 127/46 A |

FOREIGN PATENT DOCUMENTS 37-18709 12/1962 Japan.

OTHER PUBLICATIONS

Weygand et al., Uber–N Glykoside (VII), pp. 594–602.

*Primary Examiner*—Morris O. Wolk
*Assistant Examiner*—Michael S. Marcus
*Attorney, Agent, or Firm*—Armstrong, Nikaido, Marmelstein & Kubovcik

[57] ABSTRACT

One or more ketoses such as fructose are separated from a solution of sugar mixture containing the ketoses and one or more aldoses by contacting the solution of sugar mixture with an insoluble high polymer having primary amine moieties to remove the aldoses from the liquid phase by bonding the aldoses to the high polymer.

18 Claims, No Drawings

PROCESS FOR SEPARATING KETOSES AND ALDOSES

This invention relates to a process for separating one or more ketoses from one or more aldoses. More particularly, this invention relates to a process for separating one or more ketoses, e.g., fructose, from a solution of sugar mixture containing ketones and aldoses such as glucose, mannose, maltose and the like.

Sugars are usually present as a mixture either in the natural world or in chemically obtained products. For example, in the case of fructose, industrial raw materials of fructose are invert sugar obtained by hydrolysis of sucrose (cane sugar), isomerized sugar liquid obtained by isomerizing glucose or hydrolysis product of starch, and the like, but in either case, fructose is present together with glucose. Therefore, in order to obtain each sugar, it is necessary to separate each sugar from a mixture of the sugars. Concerning the separation of ketoses from aldoses, particularly separation of fructose from glucose, various methods have been proposed. Industrial scale of the separating methods can be divided into two groups. One of them is to use an inorganic compound to form a complex with sugar, for example, a complex of fructose with calcium hydroxide, calcium chloride, or the like and to separate by fractional precipitation. But the yield of this method is low and since it is necessary to demineralize the highly concentrated inorganic salt mixed in the sugar solution, this method is not easy and uneconomical.

The other method is a chromatographic separating method using ion-exchange resins. There have been proposed two methods, one of which is to use cation exchange resins of $Ca^{++}$, $Sr^{++}$, $Ba^{++}$, $Ag^+$ types and the like (U.S. Pat. Nos. 3,044,904, 3,044,905 and 3,044,906), and the other of which is to use anion exchange resins of $HSO_3^-$ and/or $SO_3^{--}$ types (U.S. Pat. No. 3,806,363). The method of using ion-exchange resins has advantages in unnecessity of converting the sugar into its derivatives and simplicity of the procedure but there are also many defects in that since selective adsorptivity and load-carrying capacity for sugars are insufficient, a large amount of the resin against the sugar to be separated should be used and a longer time is necessary for the separation. Therefore, resins having excellent selective adsorptivity and load-carrying capacity have long been desired.

It is an object of this invention to provide a process for separating ketoses and aldoses from a mixed solution of ketoses and aldoses easily and effectively by using an insoluble high polymer having excellent selective adsorptivity and load-carrying capacity.

This invention provides a process for separating one or more ketoses from a solution of sugar mixture containing one or more ketoses and one or more aldoses which comprises contacting the solution of sugar mixture with an insoluble high polymer having primary amine moieties to remove the aldoses from the liquid phase by bonding the aldoses to the high polymer.

According to this invention, since the insoluble high polymer having primary amine moieties can selectively bond to one or more aldoses, one or more ketoses retained in the liquid phase can easily separated from the sugar mixture containing the ketoses and the aldoses. In addition, the aldoses bonded to the high polymer can be recovered by releasing them from the high polymer. Therefore the aldoses can also be separated from the sugar mixture containing one or more ketoses and one or more aldoses.

The term "bonding" or "bond" used in this invention includes not only chemical bonds but also physical bonds such as adsorption by physical affinity.

The most outstanding features of the insoluble high polymer having primary amine moieties used in this invention comparing with conventional ion-exchange resins are that the insoluble high polymer can selectively bond to aldoses and further the amount of bonding is very large and the bonding rate is very fast. For example, in the case of separating fructose from an aqueous mixture of equal amounts of fructose and glucose using a conventional ion-exchange resin which is packed in a column and the aqueous mixture being added to the column from the top followed by eluting with water, the flow rate of the eluate is generally $SV = 0.2$ $hour^{-1}$ or less and the amount of the treated sugar with good separation based on the weight of the ion-exchange resin is 0.15 g/g or less. If the flow rate of aqueous sugar mixture becomes faster, separation of fructose becomes worse. On the contrary, in the case of using the insoluble high polymer having primary amine moieties according to this invention, the fructose can excellently be separated at a flow rate of $SV = 0.5$ $hour^{-1}$ with the amount of the treated sugar per weight of the high polymer of 0.3–0.4 g/g.

The high polymer used in this invention should be a solid insoluble in water, alcohols, or aqueous alcohols. The term "insoluble" means insoluble in water, alcohols or aqueous alcohols with or without swelling.

Selective bonding ability of the insoluble high polymer to aldoses is due to the primary amine moieties rather than backbone structure of the high polymer. Therefore, high polymers having various backbone structures such as carbon-carbon bonds, ether bonds, ester bonds, amide bonds, urethan bonds and the like may be used in this invention. Among these high polymers, those having carbon-carbon chain as backbone structure are particularly preferable because of chemical stability and free from hydrolysis. It is well known that high polymers having carbon-carbon chain as backbone structure can easily be obtained by polymerization of monomers having unsaturated bonds.

Examples of high polymers which form backbone structure are those having the unit:

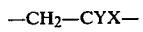

wherein X is amino, hydroxyl, carboxyl, phenyl, amide, ester, ether, halogen and the like; and Y is hydrogen, methyl and the like, more concretely, those having backbone structure of $-CH_2-CHX-$ wherein X is as defined above, such as poly(vinyl alcohol), poly(vinyl amines), poly(acrylic acid), polystyrene and the like; those having backbone structure of $-CH_2-C(CH_3)X-$, wherein X is as defined above, such as poly(isopropenyl amine), poly(methacrylic acid), poly(methacrylonitrile), and the like. Further, polysaccharides such as cellulose, agarose, starch, dextran and the like, polyamides such as a poly(amino acid) and the like can be used as backbone high polmers.

Among these high polymers, those having primary amine moieties can be used as they are, but those having no primary amine moieties should be converted to have primary amine moieties as side chains. Any conventional methods can be used so that the high polymers may have primary amine moieties.

The high polymers having primary amine moieties should be insoluble in water, alcohols or aqueous alcohols. Those which are soluble in water or aqueous alcohols should be converted into insoluble ones. If a high polymer is soluble in water or aqueous alcohols like poly(vinyl amine), separation of ketoses from aldoses cannot be accomplished even if aldoses can be bonded to the soluble high polymer. On the other hand, primary amines having low molecular weight such as aniline, propylamine, and the like cannot be used for separating ketoses from aldoses. Further, since low molecular weight primary amines are generally poisonous and sugar is used for food or medicines, the use of the low molecular weight primary amines is not preferable from a viewpoint of safety. It is the selective bonding between aldoses and the high polymer insoluble in water, alcohols or aqueous alcohols that makes the separation of ketoses in the liquid phase from the sugar mixture of aldoses and ketoses possible.

In order to make high polymers insoluble in water or aqueous alcohols or to lessen swelling of the high polymers, crosslinking of the high polymers may preferably be applied to. Crosslinking may be carried out after the polymerization or during the polymerization. Any conventional crosslinking methods may be employed in this invention. For example, a high polymer having $NH_2$ groups may be crosslinked by using tolylenediisocyanate, ethylene glycol diglycidyl ether, epichlorohydrin and the like, or such a polyfunctional monomer as divinylbenzene, ethylene glycol dimethacrylate or the like may be copolymerized during the polymerization to be crosslinked.

It is preferable to use the insoluble high polymers having 2% or more of degree of crosslinking.

Amine moieties of the insoluble high polymer should be primary amine moieties, i.e. $NH_2$ groups of primary amines. Insoluble high polymers having secondary amine moieties, tertiary amine moieties or quaternary amine moieties do not show selective bonding ability to aldoses. If the $NH_2$ group is of primary amines, any primary amines such as aliphatic, aromatic and aralkyl may have selective bonding ability to aldoses. In the case of aromatic primary amine moieties wherein the $NH_2$ group is directly bonded to an aromatic ring, it is preferable for binding to aldoses that at least a part of the $NH_2$ groups are bonded to an inorganic acid such as HCl, $H_2SO_4$ or the like or a lower fatty acid such as acetic acid to form salts thereof.

As to the positions of the primary amine moieties in the insoluble high polymer, the $NH_2$ groups may be bonded either to the backbone chain directly or to side chains.

The insoluble high polymers useful in this invention can be divided into four groups depending on the kind of primary amines as follows.

First group includes the insoluble high polymers having aliphatic primary amine moieties, in which the $NH_2$ groups of primary amine are bonded directly to the backbone chain, represented by the formula:

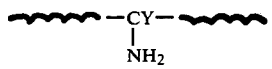

wherein Y is hydrogen or methyl. Examples of the high polymers of this group are crosslinked poly or copoly(-vinyl amines), crosslinked poly or copoly(isopropenyl amine), e.g. copolymers of styrene and/or divinylbenzene and vinyl amine, Hofmann degradation products of a polymer or copolymer of acrylamide such as copolymers of acrylamide and divinylbenzene, copolymers of acrylamide, divinylbenzene and one or more other vinyl monomers, and the like. Among them, the insoluble high polymers having the structure of polymer or copolymer of vinyl amine are preferable because of high density of the $NH_2$ groups in the polymer.

Second group includes the insoluble high polymers having aliphatic primary amine moieties, in which the $NH_2$ groups of primary amine are bonded to side chains of the polymer, represented by the formula:

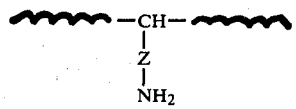

wherein Z is an aliphatic group having 1 to 6 carbon atoms. As to the bonding between the backbone chain of the high polymer and the side chain, such bonds as carbon-carbon bond, ether bond, ester bond, amide bond, acetal bond and the like may be used. For example, Z can be represented by the formulas $-(CH_2)_n-$ (n=1 to 4), $-CONHCH_2CH_2-$, $-O(CH_2)_n-$ (n=2 to 3), $-C_6H_9(OH)-$, and the like. Examples of the high polymers of this group are crosslinked polymers or copolymers of basic amino acids such as lysine; crosslinked aminoalkyl ethers of polymers having OH groups such as polysaccharides, e.g. cellulose, a polymer or copolymers of vinyl alcohol, and the like; copolymers of allylamine and divinylbenzene or copolymers of allylamine, divinylbenzene and one or more other vinyl monomers; a high polymer obtained by condensation of a polymer or copolymer of methyl acrylate with ethylenediamine; a high polymer obtained by reducing with $LiAlH_4$ a copolymer of styrene and methacrylonitrile; a high polymer obtained by reacting a high polymer containing epoxy groups, e.g. a copolymer of vinyl cyclohexene oxide and divinyl benzene, with $NH_3$; and the like.

Third group includes the insoluble high polymers having primary amine moieties, in which the $NH_2$ groups of primary amine are bonded to aromatic rings directly, represented by the formula:

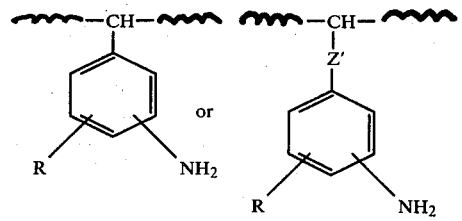

wherein R is hydrogen, methyl or nitro. The backbone chain of the high polymer may be bonded to the aromatic ring through ether bond, ester bond, amide bond and the like (designated as Z'). Examples of the high polymers of this group are a polymer or copolymer of aminostyrene or a nuclear substituted derivative thereof, an aminated polymer or copolymer of styrene, a copolymer of divinylbenzene and aminostyrene, copolymers of divinylbenzene, aminostyrene and one or more other vinyl monomers such as styrene, polymers or copolymers mentioned above wherein $NO_2$ groups or $CH_3$ groups are introduced in the benzene rings, aminobenzyl ethers of high polymers having OH groups such as polysaccharides, e.g. cellulose, or a polymer or copolymer of vinyl alcohol, aminobenzoic acid esters of the high polymers having OH groups as mentioned above, and the like.

Fourth group includes the high polymers having primary amine moieties, in which the $NH_2$ groups of primary amine are bonded to saturated side chains of aromatic rings, represented by the formula:

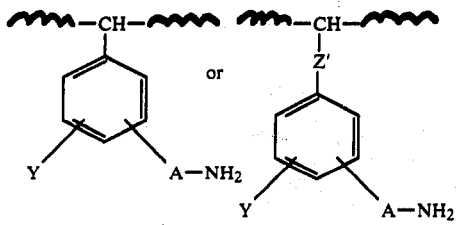

wherein Y is hydrogen or methyl; A is an aliphatic group having 1 to 2 carbon atoms such as $C_{1-2}$ alkylene or polyalkylene which may include an imino group such as $-CH_2-NH-CH_2-CH_2-$ or the like; and $Z'$ is as defined above. Examples of the high polymers of this group are a polymer or copolymer of vinyl benzylamine or a nuclear substituted derivative thereof, a copolymer of vinyl benzylamine and divinylbenzene, copolymers of vinyl benzylamine, divinylbenzene and one or more other vinyl monomers such as styrene, high polymers as mentioned above wherein $CH_3$ groups are introduced in the benzene rings, a high polymer obtained by reacting chloromethylated polystyrene with ethylenediamine, and the like.

The insoluble high polymers mentioned above can be obtained by conventional polymerization or copolymerization methods or conventional methods for introducing $NH_2$ groups of primary amine. In any case, insoluble high polymers having $NH_2$ groups of primary amine are effective in this invention.

As to the high polymers of the third group having $NH_2$ groups directly bonded to aromatic rings, it is preferable that at least a part of the $NH_2$ groups of primary amine forms salts with HCl, $H_2SO_4$, acetic acid or the like, since the bonding capacity of the free $NH_2$ group is small. The high polymers belonging to the other groups do not need to form such salts of the $NH_2$ groups. The high polymers belonging to the fourth group have a tendency to show smaller aldose bonding capacity than those belonging to the first and second groups.

The insoluble high polymers used in this invention preferably have the primary amine moieties in an amount of 0.5 meq/g or more. If the amount of the $NH_2$ groups of primary amine is too small, the insoluble high polymer has poor practical value due to small capacity to bond to aldoses. The larger the amount of the $NH_2$ groups becomes, the more the amount of bonded aldoses increases. But if the amount of the $NH_2$ groups is too much, swelling of the high polymer against water also increases unfavorably. Therefore, the high polymer usually contains the $NH_2$ groups in 23 meq/g or less, more preferably 15 meq/g or less.

As the ketoses, there may be used ketohexoses such as fructose and sorbose, and ketopentoses such as ribulose and xylulose.

As the aldoses, there may be used not only monosaccharides such as aldohexoses, e.g. glucose, galactose, mannose, etc., aldopentoses, e.g. ribose, xylose, arabinose, etc., aldotetroses and aldotriose but also oligosaccharides having aldose type reducing groups, maltose, maltotriose and the like.

The sugar mixture which can be used in this invention is a mixture of one or more ketoses and one or more aldoses. Since aldoses including aldose type oligosaccharides can selectively be bonded to the insoluble high polymer having primary amine moieties, the process of this invention can widely be applied to separation of one or more ketoses from the sugar mixture containing one or more ketoses and one or more aldoses. Particularly, the process of this invention can preferably be applied to separation of fructose from a solution of sugar mixture of fructose and aldose type sugars such as glucose, mannose, maltose and the like, for example, an invert sugar solution, an isomerized sugar solution resulting from isomerization of glucose or saccharification products of starch, a solution in which fructose ratio is increased by fractionation by producing a complex of glucose with NaCl, and the like.

The sugar mixture usually uses water as a solvent mainly from economical point of view. But lower alcohols such as ethanol or aqueous lower alcohols can be used as a solvent considering procedures after the separation such as crystallization step.

The solution of sugar mixture is contacted with the insoluble high polymer preferably at a temperature of 10° to 80° C., more preferably 30° to 70° C. The higher the temperature is, the faster the bonding rate becomes, but there is a fear of decomposition and coloring of the sugars. If the temperature is too low, viscosity of the solution of sugar mixture becomes larger and handling of the solution of sugar mixture becomes difficult.

The contact of the solution of sugar mixture with the insoluble high polymer is made preferably at a pH of 3 to 10 in the case of the high polymers belonging to the first, second and fourth groups, while the contact is preferable at an acidic side in the case of the third group high polymers.

As to the method for contacting the solution of sugar mixture with the insoluble high polymer, any conventional methods generally used for adsorption and separation may be used. For example, there may be used a method in which the solution of sugar mixture and an eluate, in this order, flow through a column which has been packed with the insoluble high polymer in the same way as the case of using an ion-exchange resin and a ketose is taken out, or a method in which the sugar mixture is contacted with the insoluble high polymer in a tank, and the like.

Since the ketoses are not bonded to the insoluble high polymer or only a small amount of the ketoses are bonded to the high polymer comparing with the aldoses even if bonded, the ketoses are separated from the aldoses by recovering the former from the liquid phase.

The aldoses bonded to the insoluble high polymer can be released or desorbed by water or an aqueous alcohol. If the high polymer having the $NH_2$ groups of an aliphatic primary amine or of an aromatic primary amine in which the $NH_2$ groups are bonded to saturated side chains of aromatic rings is used, the aldoses can easily be released or desorbed by an eluate of pH 5 or less, preferably pH 3–5 and can be recovered almost quantitatively. If the high polymer belonging to the third group in which the $NH_2$ groups are directly bonded to aromatic rings is used, release the aldoses is difficult and preferably carried out pH 3 or less.

The higher the release temperature is, the faster the release rate becomes, but there is a fear of decomposition and coloring if the temperature is too high. The release is conducted preferably at a temperature of 10° to 80° C., more preferably 30°-70° C.

After the release of the aldoses, the insoluble high polymer can be used again and again for separating the ketoses from the sugar mixture.

In the following examples, amounts of sugars bonded to the insoluble high polymers are measured in order to show easiness of separating ketoses from aldoses. In practical separating processes, a procedure of separating one or more ketoses from the sugar mixture is repeated until only the ketoses can be taken out of the sugar mixture.

EXAMPLE 1

In a test tube, 0.5 g of crosslinked poly(vinyl benzylamine) obtained by amination of a copolymer of chloromethylstyrene and divinylbenzene by Delepine reaction having an HCL adsorption capacity of 3.8 meq/g was placed and 10 ml of an aqueous solution dissolving 0.1 g of glucose and 0.1 g of fructose was added to the test tube. The test tube was heated to 70° C. After 30 minutes, the amounts of glucose and fructose in the aqueous solution were determined to calculate the amounts of bonded sugars.

The copolymer of chloromethylstyrene and divinyl benzene was prepared by polymerizing 50 g of chloromethylstyrene and 1 g of divinylbenzene in 150 g of water using 0.25 g of azobisisobutyronitrile at 70° C. for 7 hours.

The HCl adsorption capacity corresponds to the amount of the $NH_2$ groups in a high polymer and was measured as follows.

To 0.5 g of a high polymer, 25 ml of 0.1 N HCl was added and allowed to stand for 20 hours at room temperature. After filtration and washing with water, the filtrate was combined with the washed solution to make 50 ml of solution. 20 Ml of the solution was taken and titrated with 0.05 N NaOH to determine a HCl adsorption capacity of the polymer. If a HCl adsorption capacity of a polymer is 4.5 meq/g or more, 0.2 N HCl is used.

The results are as shown in Table 1. As is clear from Table 1, the high polymer can selectively bond to glucose but it hardly bonds to fructose.

COMPARATIVE EXAMPLE 1

The procedure of Example 1 was repeated except for using poly(vinyl N-methylbenzylamine) having secondary amine moieties (HCl adsorption capacity 1.9 meq/g) in place of the high polymer having primary amine moieties. The results are as shown in Table 1. As is clear from Table 1, the high polymer having secondary amine moieties does not bond to glucose and fructose.

COMPARATIVE EXAMPLE 2

The procedure of Example 1 was repeated except for using a weakly basic ion-exchange resin Amberlite IR-93 (trade-mark, Rohm & Haas Co.) having tertiary amine moieties, $-N(CH_3)_2$, in place of the high polymer having primary amine moieties. The results are as shown in Table 1. As is clear from Table 1, the high polymer having tertiary amine moieties does not bond to glucose and fructose.

Table 1

| Example No. | Type of amine moieties | Amounts of sugars bonded to the high polymer | |
|---|---|---|---|
| | | Glucose (mg/g . polymer) | Fructose (mg/g . polymer) |
| Example 1 | $-NH_2$ | 53 | 1 |
| Comparative Example 1 | $-NHCH_3$ | 0 | 0 |
| Comparative Example 2 | $-N(CH_3)_2$ | 0 | 0 |

EXAMPLES 2–12

Using the insoluble high polymers having primary amine moieties as listed in Table 2, the procedure of Example 1 was repeated.

Table 2

| Example No. | High polymer | HCl adsorption capacity (meq/g) |
|---|---|---|
| 2 | Poly(vinyl amine)*[1] | 4.6 |
| 3 | Poly(isopropenyl amine)*[1] | 2.7 |
| 4 | Aminopropyl ether of poly(vinyl alcohol)*[1] | 3.8 |
| 5 | Aminoethyl amide of poly(acrylic acid)*[1] | 4.3 |
| 6 | Aminoethyl ether of cellulose*[1] | 0.8 |
| 7 | Polylysine*[1] | 4.6 |
| 8 | Copoly(styrene-methallylamine) | 3.0 |
| 9 | Aminobenzyl ether of poly(vinyl alcohol)*[1] | 2.2 |
| 10 | Copoly(p-amino styrene-divinylbenzene) | 6.2 |
| 11 | Aminated copoly(vinyl toluene-divinylbenzene) | 1.7 |
| 12 | Amino methylated copoly(vinyl toluene-divinylbenzene) | 1.7 |

Note)
*[1] The high polymer was crosslinked by using 2,4-tolylenediisocyanate, the amount of NCO of which corresponds to 20% of the $NH_2$ groups in the high polymer.

The high polymers listed in Table 2 were prepared by conventional processes. Since the desired reaction accompanies side reactions in each step, the high polymer produced usually has various structures due to the side reactions in addition to the normal structure. Therefore HCl adsorption capacity is measured to indicate the $NH_2$ content.

The results are as shown in Table 3.

Table 3

| Ex. No. | Type of primary amine moieties* | Amounts of sugars bonded to the high polymer | |
|---|---|---|---|
| | | Glucose (mg/g . polymer) | Fructose (mg/g . polymer) |
| 2 | $A-NH_2$ | 128 | 6 |
| 3 | $A-NH_2$ | 68 | 0 |
| 4 | $A-O-(CH_2)_3-NH_2$ | 91 | 1 |
| 5 | $A-CONH-(CH_2)_2-NH_2$ | 106 | 4 |
| 6 | $A-O-(CH_2)_2-NH_2$ | 21 | 5 |
| 7 | $A-(CH_2)_4-NH_2$ | 125 | 2 |
| 8 | $A-CH_2-NH_2$ | 73 | 0 |
| 9 | 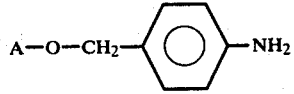 | 12 | 0 |
| 10 | 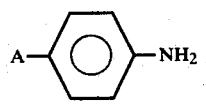 | 11 | 0 |

Table 3-continued

| Ex. No. | Type of primary amine moieties* | Amounts of sugars bonded to the high polymer | |
|---|---|---|---|
| | | Glucose (mg/g . polymer) | Fructose (mg/g . polymer) |
| 11 | A—⬡(NH₂)(CH₃) | 11 | 0 |
| 12 | A—⬡(CH₂—NH₂)(CH₃) | 26 | 0 |

Note)
*A means backbone chain.

EXAMPLES 13–18

Bonding of sugars to insoluble high polymers in which the NH₂ groups of primary amine are converted to HCl or acetic acid salts was examined. The same poly(vinyl amine) as used in Example 2 and the same copoly(p-amino styrene-divinylbenzene) as used in Example 10 were used as shown in Table 4. The same procedure as used in Example 1 was used in these Examples. The results are as shown in Table 4.

Table 4

| Example No. | High copolymer | Proportion of salt of NH₂ in the whole NH₂ groups (%) | Amounts of sugars bonded to the high polymer | |
|---|---|---|---|---|
| | | | Glucose (mg/g. polymer) | Fructose (mg/g. polymer) |
| 13 | Poly(vinyl amine) | 0 | 130 | 5 |
| 14 | " | 50* | 105 | 2 |
| 15 | " | 100* | 38 | 0 |
| 10 | Copoly(p-amino styrene-divinylbenzene) | 0 | 11 | 0 |
| 16 | " | 50* | 75 | 0 |
| 17 | " | 100* | 82 | 0 |
| 18 | " | 100** | 80 | 0 |

Note)
*HCl salt
**Acetate

EXAMPLES 19–26

To 0.5 g of copoly(vinyl amine-divinylbenzene) (HCl adsorption capacity 3.3 meq/g), 20 ml of an aqueous solution dissolving 0.125 g of sugars as listed in Table 5 was added and heated at 70° C. for 1 hour. Amount of sugar bonded to the insoluble high polymer is as shown in Table 5.

Table 5

| Example No. | Sugar | Amount of sugar bonded to the high polymer (mg/g . polymer) |
|---|---|---|
| 19 | Mannose | 77 |
| 20 | Galactose | 82 |
| 21 | Xylose | 81 |
| 22 | Ribose | 85 |
| 23 | Arabinose | 85 |
| 24 | Maltose | 61 |
| 25 | Sorbose | 2 |
| 26 | Glyceraldehyde | 130* |

Note)
*The polymer was colored and the reaction was somewhat different from those of Examples 19 to 25.

EXAMPLES 27 AND 28

The procedure of Example 19 was repeated except for using aqueous ethanol (EtOH 80% by volume) or ethanol in place of water. The results are as shown in Table 6.

Table 6

| Example No. | Solvent | Amount of sugar bonded to the high polymer (mg/g . polymer) |
|---|---|---|
| 27 | Ethanol - H₂O | 110 |
| 28 | Ethanol | 85 |

EXAMPLES 29–33

In a test tube equipped with a stopper, 0.5 g of poly(-vinyl amine) obtained by Hofmann degradation of a copolymer of acrylamide and divinylbenzene (molar ratio 90:10) having an HCl adsorption capacity 4.8 meq/g was placed and 10 ml of a buffer solution (pH 2–10.2) dissolving 0.1 g of glucose and 0.1 g of fructose was added to the test tube. The test tube was agitated in a thermostat maintained at 70° C. for 30 minutes. Then the amounts of glucose and fructose in the buffer solution were determined to calculate the amounts of bonded sugars.

The results are as shown in Table 7.

Table 7

| Example No. | pH of the sugar mixture | Amounts of sugars bonded to the high polymer | |
|---|---|---|---|
| | | Glucose (mg/g . polymer) | Fructose (mg/g . polymer) |
| 29 | 10.2 | 123 | 4 |
| 30 | 6.9 | 148 | 12 |
| 31 | 5.0 | 132 | 5 |
| 32 | 3.5 | 115 | 0 |
| 33 | 2.0 | 98 | 0 |

EXAMPLES 34 AND 35

The procedure of Example 31 was repeated except for changing the temperature to 50° C. (Example 34) or 30° C. (Example 35). The amount of glucose bonded to the high polymer was 105 mg/g.polymer at 50° C. and 62 mg/g. polymer at 30° C.

EXAMPLE 36

A copolymer was obtained by polymerizing 25 g of acrylamide and 10 g of divinylbenzene in 125 ml of dioxane using 0.2 g of azobisisobutyronitrile at 70° C. for 6 hours. The copolymer was subjected to Hofmann degradation to afford crosslinked poly(vinyl amine) having HCl adsorption capacity of 4.4 meq/g. A double-walled column having inner diameter of 1.2 cm was packed with 10 g of the crosslinked poly(vinyl amine) and heated to 60° C. 4 Grams of isomerized sugar solution obtained by acting a glucose isomerase on a saccharification solution of starch (sugar concentration 50% (w/w); sugar composition, fructose 42%, glucose 50% and oligosaccharides 8%) was fed to the column from the top, and the column was eluted with 60 ml of distilled water followed by an acetic acid buffer solution of pH 4. The flow rate was 60 ml/hour and fraction was made with each 5 ml. The amounts of sugars in each fraction were determined and listed in Table 8.

Table 8

| Fraction number | Amounts of sugars | | |
|---|---|---|---|
| | Fructose (mg/ml) | Glucose (mg/ml) | Oligo-saccharides (mg/ml) |
| 16 | 0 | 0 | 0 |
| 18 | 1 | 0 | 0 |
| 19 | 12 | 0 | 0 |
| 20 | 35 | 0 | 0 |
| 21 | 50 | 0 | 0 |
| 22 | 38 | 0 | 0 |
| 23 | 19 | 0 | 0 |
| 24 | 8 | 1 | 1 |
| 25 | 2 | 2 | 4 |
| 26 | 0 | 10 | 12 |
| 27 | 0 | 17 | 10 |
| 28 | 0 | 28 | 4 |
| 29 | 0 | 30 | 0 |
| 30 | 0 | 27 | 0 |
| 31 | 0 | 26 | 0 |
| 32 | 0 | 24 | 0 |
| 33 | 0 | 13 | 0 |
| 34 | 0 | 10 | 0 |
| 35 | 0 | 5 | 0 |
| 36 | 0 | 2 | 0 |

COMPARATIVE EXAMPLE 3

A column as used in Example 36 was packed with poly(vinyl amine) not crosslinked. Using the same conditions as in Example 36, the isomerized sugar solution was intended to be separated but the experiment was impossible because the polymer was almost dissolved.

EXAMPLE 37

A double-walled column having inner diameter of 0.9 cm was packed with 1.4 g of the same crosslinked poly(vinyl benzylamine) as used in Example 1, and heated to 70° C. To the column, 0.4 ml of an aqueous sugar solution containing 20 mg of mannose and 20 mg of fructose was added and eluted with water. The flow rate was 18 ml/hour and fraction was made with each 2.4 ml. The amounts of sugars in each fraction were determined and listed in Table 9. The mannose not eluted until fraction number 8 was eluted with 0.2 N HCl.

Table 9

| Fraction number | Amounts of sugars | |
|---|---|---|
| | Fructose (mg) | Mannose (mg) |
| 1 | 0 | 0 |
| 2 | 0.1 | 0 |
| 3 | 5.9 | 0.7 |
| 4 | 7.9 | 1.2 |
| 5 | 4.0 | 0.6 |
| 6 | 0.9 | 0.3 |
| 7 | 0.5 | 0.2 |
| 8 | 0 | 0.2 |

What is claimed is:

1. A process for separating one or more ketoses from a solution of sugar mixture containing one or more ketoses and one or more aldoses which comprises contacting the solution of sugar mixture with a high polymer having primary amine moieties and which is insoluble in water, alcohols or aqueous alcohols to remove the aldoses from the liquid phase by bonding of the aldoses to the high polymer.

2. A process according to claim 1, wherein the primary amine moieties are NH$_2$ groups of aliphatic primary amines.

3. A process according to claim 1, wherein the primary amine moieties are NH$_2$ groups of aromatic primary amines.

4. A process according to claim 1, wherein the primary amine moieties are NH$_2$ groups of aralkyl primary amines.

5. A process according to claim 1, wherein the insoluble high polymer has the NH$_2$ groups of primary amine bonded to backbone chain represented by the formula:

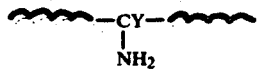

wherein Y is hydrogen or methyl.

6. A process according to claim 1, wherein the insoluble high polymer has the NH$_2$ groups of primary amine bonded to side chains of the polymer represented by the formula:

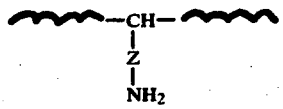

wherein Z is an aliphatic group having 1 to 6 carbon atoms.

7. A process according to claim 6, wherein Z is a group of the formula —(CH$_2$)$_n$—, wherein n is an integer of 1 to 4, —CONHCH$_2$CH$_2$—, —O(CH$_2$)$_n$—, wherein n is 2 or 3, or —C$_6$H$_9$(OH)—.

8. A process according to claim 1, wherein the insoluble high polymer has the NH$_2$ groups of primary amine bonded to aromatic rings directly represented by the formula:

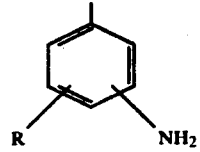

wherein R is hydrogen, methyl or nitro.

9. A process according to claim 1, wherein the insoluble high polymer has the NH$_2$ groups of primary amine bonded to saturated side chains of aromatic rings represented by the formula:

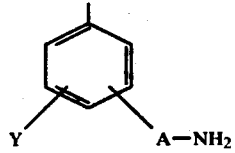

wherein Y is hydrogen or methyl; and A is an aliphatic group having 1 to 2 carbon atoms or polyalkylene which may include an imino group.

10. A process according to claim 1, wherein at least a part of the primary amine moieties form salts with an inorganic acid or a lower fatty acid.

11. A process according to claim 1, wherein the ketose is a ketohexose, a ketopentose or a mixture thereof.

12. A process according to claim 1, wherein the aldose is an aldohexose, an aldopentose, an aldotetrose, an aldotriose, an oligosaccharide having aldose type reducing group, or a mixture thereof.

13. A process according to claim 1, wherein the sugar mixture is a mixture of fructose and glucose.

14. A process according to claim 1, wherein the sugar mixture is a mixture of fructose, glucose, mannose, maltose and maltotriose.

15. A process according to claim 1, wherein the sugar mixture contains water as a solvent.

16. A process according to claim 1, wherein the sugar mixture contains an alcohol or an aqueous alcohol as a solvent.

17. A process according to claim 1, wherein the contact of the sugar mixture with the insoluble high polymer is carried out at a temperature of 10° to 80° C.

18. A process according to claim 1, which further comprises releasing the aldoses bonded to the insoluble high polymer from the insoluble high polymer with water or an aqueous alcohol at a temperature of 10° to 80° C.

* * * * *